(12) United States Patent
Yang et al.

(10) Patent No.: US 9,415,138 B2
(45) Date of Patent: Aug. 16, 2016

(54) DYNAMIC MACROPORE FORMATION USING MULTIPLE POROGENS

(71) Applicant: Board of Trustees of the Leland Stanford Junior University, Palo Alto, CA (US)

(72) Inventors: Fan Yang, Palo Alto, CA (US); Li-Hsin Han, Palo Alto, CA (US); Xinming Tong, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 132 days.

(21) Appl. No.: 13/970,456

(22) Filed: Aug. 19, 2013

(65) Prior Publication Data
US 2014/0161843 A1 Jun. 12, 2014

Related U.S. Application Data

(60) Provisional application No. 61/691,511, filed on Aug. 21, 2012.

(51) Int. Cl.
*A61L 27/56* (2006.01)
*A61L 27/38* (2006.01)
*A61L 27/22* (2006.01)

(52) U.S. Cl.
CPC ............... *A61L 27/56* (2013.01); *A61L 27/38* (2013.01); *A61L 2400/08* (2013.01)

(58) Field of Classification Search
None
See application file for complete search history.

(56) References Cited

U.S. PATENT DOCUMENTS

| 6,197,586 | B1* | 3/2001 | Bhatnagar | A61L 27/3817 424/93.21 |
|---|---|---|---|---|
| 2011/0311746 | A1* | 12/2011 | Ma et al. | 428/36.91 |
| 2013/0173014 | A1* | 7/2013 | Mikos et al. | 623/23.63 |
| 2014/0017284 | A1* | 1/2014 | Yang et al. | 424/400 |

FOREIGN PATENT DOCUMENTS

WO 2010046084 4/2010

OTHER PUBLICATIONS

Chen, Ying-Chieh; et al. "Functional Human Vascular Network Generated in Photocrosslinkable Gelatin methacrylate hydrogels" Advanced Functional Materials, 2012, 22, 2027-2039.*
Dumitru, editor; "Polymeric Biomaterials, Revised and Expanded", 2nd edition, Marcel Dekker, 2002, p. 336, Controls section.*

* cited by examiner

*Primary Examiner* — Sue Liu
*Assistant Examiner* — Erin Hirt
(74) *Attorney, Agent, or Firm* — Richard Aron Osman; Isaac Rutenberg (57) ABSTRACT

Macroporous 3-D tissue engineering scaffold are manufactured by contacting an article comprising multiple distinct macroparticulate porogens distributed within a polymer scaffold, wherein the porogens are selectively and sequentially dissolvable by corresponding biocompatible stimuli.

20 Claims, 5 Drawing Sheets

DYNAMIC MACROPORE FORMATION USING MULTIPLE POROGENS

CROSS-REFERENCE

This application is a continuation of Ser No. 61/691,511; filed Aug. 21, 2012.

INTRODUCTION

Macropores, the pore spaces larger than the typical size of cells (5-20 μm), are an important feature to cell-based therapies that utilize three-dimensional (3D) tissue engineering scaffolds [1-9]. Macropores in tissue engineering scaffold facilitate tissue formation by providing free space for desirable bioactivities for tissue formation, including vascularization, cell proliferation and the cell production of extracellular matrix (ECM) components [10], while offering ample internal surface area to assist cell migration and provide cells physical support.

Step-wise, dynamic macropore formation is another important feature that allows tissue engineering scaffolds to generate new macropores during the procedure of tissue formation. Such new macropores are produced in comply with the pace of cell proliferation and tissue formation, as the ECM that the cells generate gradually replace the biochemical and mechanical functions of the lost scaffold volume.

Current technology for fabricating macroporous scaffolds involves two different categories: (1) "top-down" approaches, which create macropores in a bulk volume; and (2) "bottom-up" approaches, which build macroporous structure directly by assembling biopolymers or small molecules. Commonly used top-down approaches include template-assisted macropore-formation, such as salt-based [1], polymer-based [2] and emulsion-based [3] pore-leaching, and phase separation, such as gas foaming [4] and freeze drying [5]. The bottom-up approaches include electrospinning [6], stereolithography [7-8, 11], and 3D printing [9]. The top-down approaches are widely used for tissue engineering due to their low-cost and scalable fabrication methods. The bottom-up approaches, on the other hand, offer higher controllability over the shape, size and alignment of macropores. However, most current methods for making macroporous scaffolds lack two important features for tissue engineering applications: (1) cell-friendly macropore-formation, and (2) step-wise, temporally controllable dynamic macropore-formation.

Cell-friendly Macropore-formation: Most of the current methods to fabricate macroporous scaffolds (top-down and bottom-up) involve the use of organic solvents, excess heat, high stress and harsh pH values, which are not cell-friendly. Therefore, cells can only be seeded onto the macroporous scaffolds after the fabrication process, and left to grow into the macropores over time. Such processes often lead to poor cell distribution and shallow cell penetration, which makes it difficult for applying macroporous scaffolds to engineer tissues with clinically relevant dimensions.

Step-wise, Temporally Controllable Macropore-formation: Upon implantation, therapeutic cells seeded in macroporous scaffolds are often subject to the mechanical stress from the surrounding tissues and inflammatory responses [12]. Therefore, it is desirable to have a scaffold that physically protects the cells at the early stage post-transplantation. Meanwhile, as the cells deposit their own ECM overtime, it would be beneficial for the scaffold to degrade and offer additional macroporosity to accommodate cell proliferation and new matrix formation. Using biodegradable polymers [13-15] allow accommodating such need to some extent, but biodegradation does not allow easy control of timing and extent of macropore-formation based on the pace of tissue formation.

We have created and disclose 3D tissue engineering scaffolds with dynamic, temporally and spatially controllable macropore-formation. Our invention satisfies several highly desirable functions of tissue engineering scaffolds including: (1) a cell-friendly process and allows substantially uniform encapsulation of cells in 3D; (2) provide initial protection to the transplanted cells; (3) allows dynamic, stimuli-responsive macroporosity formation to accommodate blood vessel ingrowth, cell proliferation, migration, and new matrix deposition over time.

Relevant art includes U.S. Pat. No. 7,575,759, WO2008100534, WO2008154030, WO2010046084, W)2012005783.

SUMMARY OF THE INVENTION

The invention provides macroporous 3-D tissue engineering scaffolds, articles for manufacturing such scaffolds, and related methods of making and using. The invention encompasses all combinations of particular embodiments.

In one aspect the invention provides methods for manufacturing a macroporous 3-D tissue engineering scaffold, comprising in order steps: (a) contacting an article comprising first, second and optionally third macroparticulate porogens distributed within a polymer scaffold, wherein the first porogens are selectively dissolvable by a first biocompatible stimulus, the second porogens contain living cells and are dissolvable by a second biocompatible stimulus but not by the first stimulus, and the third porogens are selectively dissolvable by a third biocompatible stimulus but not by the first stimulus nor by the second stimulus, optionally wherein the first porogens dissolve; (b) contacting the article with the second stimulus, optionally wherein the second porogens dissolve; and optionally (c) contacting the article with the third stimulus wherein the third porogens dissolve, wherein the macroporous 3-D tissue engineering scaffold is formed.

In various particular embodiments:
- the article comprises the third macroparticulate porogens distributed within the scaffold, and the method comprises the step (c) of contacting the article with the third stimulus wherein the third porogens dissolve.
- a) the cells are substantially uniformly distributed though the scaffold, b) the distribution of the cells within the scaffold is unachievable by cell migration from its surface; and/or c) the density of the cells does not decrease with distance from the surface;
- the scaffold is at least 1 cm³.
- the scaffold comprises bioactive ligands that specifically interact with biomolecules of the cells or bind biomolecules that interact with the biomolecules of the cells, to direct cell fate or induce the cells to form a tissue.
- the porogens have the shape of a sphere, an ellipsoid, a polyhedron, a cube, a rod, a cylinder, a sheet, a fiber, a ribbon, a helix, or a ring.

The porogens may be used as cell delivery vehicles to release cells at specific timing The porogens may serve as drug delivery vehicles for encapsulating and controlled release of soluble signals such as proteins, nucleic acids, and small molecules.
- the polymer is a natural polymer (e.g., a protein, a polypeptide, a polynucleotide, a natural resin, a rubber, or a polysaccharide), a synthetic polymer (e.g., poly (ethylene glycol), polystyrene, polypropylene, polyvinyl chloride, polyether, polyester, polyamide, polyimide, or organosilicon compound), or a combination.

the polymer is a natural polymer selected from fibrin, fibrinogen, fibronectin, collagen, gelatin, dextran, chondroitin sulfate, alginate, chitosan, chitin, hyaluronic acid, heparin sulfate, a protein derivative, a nucleotide, a polysaccharide, or a glycosaminoglycan.

the polymer is synthetic polymer selected from poly (ethylene glycol), poly(lactic-co-glycolic acid), poly (glycolic acid), poly (lactic acid), polycaprolactone, poly (methyl methacrylate), polyurethane, or a silicone.

each stimulus is a change in one or more of temperature, pH, ionic strength, electromagnetic radiation (e.g. ultraviolet light, infrared light, visible light, radio-frequency, alpha-ray, gamma ray, etc.) exposure, enzyme activity (adding enzyme, cofactor or inhibiting inhibitor), chelator activity, mechanical agitation, etc.

each of the porogens comprises gelatin (e.g. methacrylated Type-B), hyaluronic acid (e.g. methacrylated), or alginate (e.g., calcium alginate).

the macroporous 3-D tissue engineering scaffold comprises macropores having average pore size in the range 10-500 μm.

the scaffold is saturated with a cell growth medium.

the scaffold is shaped as an implant.

the scaffold is loaded with a drug and shaped as drug distribution vehicle.

the method further comprising the step of implanting the macroporous 3-D tissue engineering scaffold in a body.

the scaffold has one or more physical properties:

a) the scaffold has a density in the range 2.5 to 10% (wt/v);

b) the scaffold has a tunable compressive modulus from 0.3 kPa to 100 kPa c) the scaffold sustains 90% strain and 35 MPa stress without failing;

d) the scaffold maintains more than 50% strain energy after being exposed to 60, 70% cyclic compressions, e) the scaffold maintains more than 50% compressive modulus at 20-30% strain after receiving 80% cyclic compressions;

e) the scaffold visually reverses to its original shape after receiving 90% cyclic-strain; and/or f) as compression on the scaffold increases up to 90%, the density increases, and the compressive modulus of the scaffold increases non-linearly from 20 kPa to 35,600 kPa.

also distributed within the scaffold is a fibrous material (e.g., nanofibers, microfibers, or microribbons) which enhances the mechanical strength of the article.

In another aspect the invention provides a macroporous 3-D tissue engineering scaffold as made by a disclosed method.

In another aspect the invention provides an article for manufacturing a macroporous 3-D tissue engineering scaffold, said article comprising first and second macroparticulate porogens distributed within a scaffold, wherein the first porogens are selectively dissolvable by a first biocompatible stimulus, and the second porogens contain living cells and are dissolvable by a second biocompatible stimulus but not by the first stimulus.

DESCRIPTION OF PARTICULAR EMBODIMENTS OF THE INVENTION

Macroporous 3-D tissue engineering scaffold are manufactured by contacting an article comprising multiple distinct macroparticulate porogens distributed within a polymer scaffold, wherein the porogens are selectively and sequentially dissolvable by corresponding biocompatible stimuli.

In one aspect the invention provides methods for manufacturing a macroporous 3-D tissue engineering scaffold, comprising in order steps: (a) contacting an article comprising first, second and optionally third macroparticulate porogens distributed within a polymer scaffold, wherein the first porogens are selectively dissolvable by a first biocompatible stimulus, the second porogens contain living cells and are dissolvable by a second biocompatible stimulus but not by the first stimulus, and the third porogens are selectively dissolvable by a third biocompatible stimulus but not by the first stimulus nor by the second stimulus, wherein the first porogens dissolve; (b) contacting the article with the second stimulus wherein the second porogens dissolve; and optionally (c) contacting the article with the third stimulus wherein the third porogens dissolve, wherein the macroporous 3-D tissue engineering scaffold is formed.

The porogens and cells may be variously distributed within the polymer in various forms and degrees of uniformity or homogeneity or in various forms and degrees of heterogeneity. The methods can provide cell distributions unachievable by methods which rely on cell invasion. For example in particular embodiments a) the cells are substantially uniformity distributed though the scaffold, b) the distribution of the cells within the scaffold is unachievable by cell migration from its surface; and/or c) the density of the cells does not decrease with distance from the surface. In particular embodiments the cells are evenly distributed (variation less than 10 or 5%) across volumes of 0.1 or 1 mm$^3$ or along a transect or transects through the center of the scaffold.

A wide variety of cell types may be incorporated depending on the application, including mammalian cells (e.g. human), fungal cells, explanted primary or cultured cells, etc.

The scaffolds may be provided in a variety of shapes and sizes depending on the application, and the methods permit the production of cell-containing scaffolds of essentially arbitrary sizes and shapes, without constraints otherwise imposed by the need to grow the cells into the scaffold. Hence, the methods may be used to produce small, e.g. subcutaneous, drug delivering scaffolds, or large tissue replacement, e.g. femur bone. In particular embodiments, the scaffold is at least 1, 4, 8, or 16 cm$^3$. In particular embodiments the scaffold is at least 1 cm$^3$.

The scaffolds may comprises bioactive ligands that specifically interact with biomolecules of the cells or bind biomolecules that interact with the biomolecules of the cells, to direct cell fate or induce the cells to form a tissue. Some examples of suitable bioactive ligands include: carboxyl, amine, phenol, guanidine, thiol, indole, imidazole, hydroxyl, sulfate, norbornene, maleimide, laminin, fibronectin, fibrinogen, peptide sequences, or combinations thereof. The bioactive ligands may be introduced before or after dissolutions (e.g. may involve grafting new chemical groups) and may be protected groups that are de-protected via an appropriate reagent or stimulus.

The porogens may be provided in a variety of shapes and sizes, depending on the application and desired properties. For example, the porogens may have the shape of a sphere, an ellipsoid, a polyhedron, a cube, a rod, a cylinder, a sheet, a fiber, a ribbon, a helix, or a ring.

The polymer may be selected from a wide variety of suitable natural and synthetic polymers, and combinations thereof. For example, suitable natural polymers include a protein, a polypeptide, a polynucleotide, a natural resin, a rubber, or a polysaccharide. More particular examples of suitable natural polymers include from fibrin, fibrinogen, fibronectin, collagen, gelatin, dextran, chondroitin sulfate, alginate, chitosan, chitin, hyaluronic acid, heparin sulfate, a protein derivative, a nucleotide, a polysaccharide, or a glycosaminoglycan. Suitable synthetic polymers include polystyrene, polypropylene, polyvinyl chloride, polyether, polyester, polyamide, polyimide, or organosilicon compounds. More particular examples of synthetic polymers include poly (ethylene glycol), poly(lactic-co-glycolic acid), poly (glycolic acid), poly (lactic acid), polycaprolactone, poly(methyl methacrylate), polyurethane, or a silicone.

Any stimuli that are biocompatible with the cells and initiate the recited dissolution may be employed, including a change in temperature, pH, ionic strength, electromagnetic radiation (ultraviolet light, infrared light, visible light, radio-frequency wave, alpha-ray, gamma ray, etc.) exposure, enzyme activity (adding enzyme, cofactor or inhibiting inhibitor), chelator activity, mechanical agitation). etc.

The porogens may be selected from a wide variety of suitable natural and synthetic materials, and combinations thereof. Exemplary suitable porogenic materials include gelatin (e.g. methacrylated Type-B), hyaluronic acid (e.g. methacrylated), or alginate (e.g., calcium alginate).

The macroporous 3-D tissue engineering scaffold comprises macropores have cell-scale to one-order larger than cell-scale porosity, based on the incorporated cell or cells. In particular embodiments, the average pore size is in the range of 10 to 100, 300 or 500 μm. In particular embodiments the average pore size is greater than 10, 20, 40, 80, 100 or 200 μm, and/or less than 500, 300, 200, 100, 80, 40 or 20 μm.

The scaffold may be saturated with a cell growth medium. In some embodiments, the scaffolds are saturated with medium that facilitates cell growth or survival, i.e. a cell growth medium. In some embodiments, the scaffold may be impregnated with a drug or other material intended for delivery to a patient. For example, the scaffold may be intended for application on, or implantation in, the patient, and may be loaded with a drug to be delivered to the application or implantation site. Accordingly, the methods may involve applying the scaffold or implanting the scaffold onto/into a site on/in the body of a patient.

The scaffold may be provided in a variety of shapes and sizes, depending on the intended application. In a particular embodiment the scaffold is shaped as an implant.

The scaffold may loaded with various active and/or inert ingredients. In a particular application the scaffold is loaded with a drug and shaped as drug distribution vehicle.

The scaffold may be constructed to provide a variety of physical and mechanical properties. In particular embodiments the scaffold has hydrogel-like viscoelasticity, the scaffold has a density in the range 1, 1.5, 2 or 2.5 to 10, 15, 20 or 25%% (wt/v), the scaffold has a tunable compressive modulus from 0.3 kPa to 100 kPa, the scaffold sustains 50, 60 70, 80, 90% strain and 20, 30, 35 MPa stress without failing, the scaffold maintains more than 50% strain energy after being exposed to 60, 70% cyclic compression), the scaffold maintains more than 50% compressive modulus (at 20%, 30% strain) after receiving 70, 80% cyclic compressions, the scaffold visually reverses to its original shape after receiving 60, 70, 80, 90% cyclic-strain, and/or as compression on the scaffold increases up to 90%, the density increases, and the compressive modulus of the scaffold increases non-linearly from about 20 kPa to 35,600 kPa.

In particular embodiments:
a) the scaffold has a density in the range 2.5 to 10% (wt/v);
b) the scaffold has a tunable compressive modulus from 0.3 kPa to 100 kPa
c) the scaffold sustains 90% strain and 35 MPa stress without failing;
d) the scaffold maintains more than 50% strain energy after being exposed to 60, 70% cyclic compressions,
e) the scaffold maintains more than 50% compressive modulus at 20-30% strain after receiving 80% cyclic compressions;
e) the scaffold visually reverses to its original shape after receiving 90% cyclic-strain; and/or
f) as compression on the scaffold increases up to 90%, the density increases, and the compressive modulus of the scaffold increases non-linearly from 20 kPa to 35,600 kPa.

The scaffolds may comprise additional components. In particular embodiments distributed within the scaffold is a fibrous material (e.g., nanofibers, microfibers, or microribbons) which enhances the mechanical strength of the article.

In another aspect the invention provides a macroporous 3-D tissue engineering scaffold as made by a disclosed method.

In another aspect the invention provides an article for manufacturing a macroporous 3-D tissue engineering scaffold, said article comprising first and second macroparticulate porogens distributed within a scaffold, wherein the first porogens are selectively dissolvable by a first biocompatible stimulus, and the second porogens contain living cells and are dissolvable by a second biocompatible stimulus but not by the first stimulus.

The methods may comprise additional preceding and/or subsequent steps, such as the subsequent step of implanting the macroporous 3-D tissue engineering scaffold in a body.

The scaffolds are suitable for a variety of applications, including regenerative medicine and tissue engineering. The scaffolds are suitable for: a 2D/3D scaffold for in vitro cell culture/study, including cell-based drug screening in a 3D format; a 3D platform for cell culture and expansion; a 2D/3D scaffold for in vitro cell culture and subsequently in vivo implantation, such as implants for skin, fat, bone, skeletomuscular, cardiovascular, and cartilage tissues; an acellular implantation for body tissues, such as skin, fat, bone, muscle, skeletomuscular, cardiovascular, or cartilage tissue; a drug distribution vehicle; and a framework that mechanically supports a tissue engineering construct.

The scaffolds are particularly useful as tissue engineering scaffolds. Thus, they may be used to facilitate cell proliferation and tissue formation. The macroporosity is suitable to allow cellular migration, formation of intracellular matrix, supply of nutrients, angiogenesis, and the like. The scaffold material is biocompatible and, in some embodiments, biodegradable or physiologically absorbable such that the scaffold may be implanted into a body and allowed to biodegrade after a suitable period of time.

The scaffolds are a suitable biomaterial to directly encapsulate cells and to culture the cells in 3D. The scaffolds are capable of achieving relatively uniform or homogeneous distribution cells in a sizable 3D space, macroporosity for facilitating mass transport and cell growth, physical properties suitable for absorbing stress and deformation, and incorporated biochemical cues to direct cell fate. The scaffolds have highly interconnected macropores that promote nutrient diffusion and facilitate cell growth, spreading, migration and cell-cell communication and cell migration. The scaffolds exhibit large internal surface area that provides a large capacity for the proliferation of cells. The scaffolds can be customized with a broad range of stiffness, covering a range that is most relevant to tissue engineering application, such as 0 to 100 kPa. The scaffolds can sustain a large loading and deformation, and are a suitable biomaterial to regenerate load-bearing tissues, like cartilage and bones.

DESCRIPTION OF ALTERNATIVE EMBODIMENTS AND EXAMPLES

Figure 1:
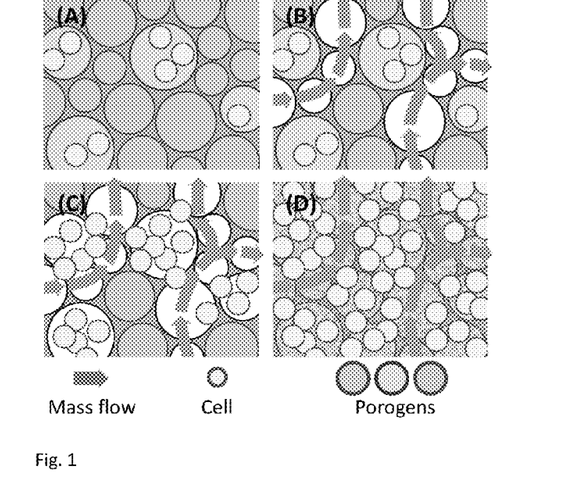
FIG. 1 Supporting tissue generation by dynamic pore formation: (A) Forming a hydrogel with multiple porogens, which encapsulate cells; (B) Removing porogen #1 to facilitate the transport of nutrient; (C) removing porogen #2 to deliver cells and facilitate cell proliferation; and (D) removing porogen #3 to further enhance cell proliferation and formation of ECM.

We have developed a new method, the "stimuli-controlled macropore-formation", to create macroporous scaffolds that satisfy the aforementioned features (FIG. 1).

To carry out controlled macropore-formation in the presence of live cell, our scheme is to fabricate a scaffold that contains microparticles of three types of hydrogels—numbered 1, 2 and 3—as the templates for macropore (porogens hereinafter) and to use cell-friendly stimuli (#1,2,3) specified for dissolving each porogen to induce macropore-formation in a step-wise manner. Cells are encapsulated by one porogen (#2) for initial protection. Our step-wise macropore-formation may be carried out as follows:

Stage 0 (FIG. 1A): The scaffold has no macropores as the porogens are in the scaffold. The cells are encapsulated in porogen #2 and physically protected.

Stage 1 (FIG. 1B): Initial macropores are formed as the porogen #1 dissolves in the presence of stimulus #1. This facilitates the nutrient diffusion throughout the scaffold, which is important to cell viability.

Stage 2 (FIG. 1C): At certain time point, cells are delivered into the scaffold matrix after stimulus #2 is applied to induce the dissolving of porogen #2. The free space left by porogen #1 and #2 can facilitate the proliferation of cells.

Stage 3 (FIG. 1D): After the cells proliferate and have produced substantial amount of ECM components in the scaffold, stimulus #3 is applied to cause porogen #3 dissolves and open more free space for cell proliferation and ECM production.

Figure 2:
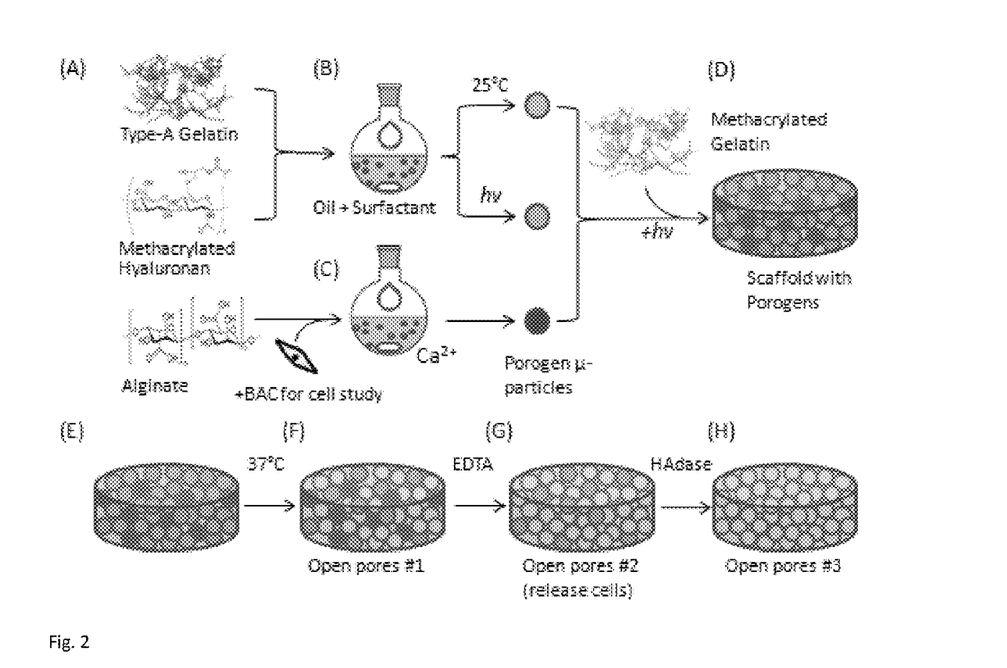
FIG. 2. Experimental scheme for controlled macropore-formation.

Our scaffold with controlled macropore-formation is cell-friendly, capable to generate macropores in a stepwise manner, and able to significantly enhance cell-proliferation and ECM production. In an example we fabricated the porogen #1, 2 and 3 from type-A gelatin, alginate and hyaluronan, which are hydrogels commonly used for tissue-engineering [16-18] (FIG. 2A-C). The stimuli for porogen removal were temperature change, small molecule chelating, and enzyme digestion (FIG. 2E-H). The backbone for the scaffold (non-dissolvable part) was made from a photocrosslinkable derivative of type-B gelatin [16] (FIG. 2D). Neonatal bovine articular chondrocytes (BACs) were encapsulated in alginate porogen for controlled cell-delivery. Acellular and cell-laden scaffolds were fabricated and tested. Morphology changes upon macropore-formation were measured using the acellular scaffolds. The effects of macropore-formation to cell-proliferation and ECM production in the cell-laden scaffold were monitored and quantified at multiple time points.

Our invention encompasses the following aspects.

Aspect 1: A Tissue Engineering Scaffold with Tunable Macroporosity.

In a first aspect, our invention is a Tissue Engineering Scaffold with Tunable Macroporosity. Such scaffold contains at least one porogen, which dissolves in the presence of a stimulus and leaves behind macropores in the scaffold.

More Details:

The tissue engineering scaffold can be made of a polymer.

The polymer can be one natural polymer, such as a protein, a polypeptide, a polynucleotide, a natural resin, a rubber, or a polysaccharide.

The polymer can be one synthetic polymer, such as polystyrene, polypropylene, polyvinyl chloride, polyether, polyester, polyamide, polyimide, or organosilicon compound.

The tissue engineering scaffold can be formed by crosslinking the polymer under a biocompatible stimulation, and thus the polymer units can encapsulate cells directly during the formation of scaffold, allowing the control of cell distribution in the scaffold.

The porogen can encapsulate a biological cell and deliver the cell upon dissolving.

The porogen can have a shape selected from a sphere, a cylinder, a ribbon, a fiber, a cube, a polyhedron, and a ring.

The porogen can be made of a natural polymer and the stimulus can be an enzyme that digests such natural polymer.

The porogen can be made of a temperature-sensitive polymer and the stimulus can be specific range of temperature.

The porogen can be made of a pH-sensitive polymer and the stimulus can be specific range of pH value.

The porogen can be made of a polyelectrolyte stabilized by an ion and the stimulus can be a molecule which carries away such ion.

Aspect 2: A Method to Remodel Extracellular Microenvironment in a Tissue Engineering Scaffold In a second aspect, our invention is a Method to Remodel Extracellular Microenvironment in a Tissue Engineering Scaffold. The remodeling creates macroporosity that supports cell viability and also the bioactivities for tissue formation, such as cell migration and production of ECM. Our method includes the following steps:

Prepare a polymer precursor.

Prepare at least one porogen, which dissolves in the presence of a least one stimulus.

Mix at the porogen in the polymer precursor, forming a scaffold paste.

Crosslink the scaffold paste and thereby creating the scaffold.

Apply the stimulus to dissolve the porogen.

Furthermore, the step (2) can be carried out with encapsulating living cells in the porogen.

Exemplary Experimental Procedures

1. Materials and Methods 1.1 Synthesis of Methacrylated Type-B Gelatin (GelB-MA)

Type B gelatin was modified with methacrylate function groups following existing protocol [16]. Type-B gelatin (GelB) was dissolved in 50° C., 100 mL, DPBS (pH=7.4) in a 250 mL round bottom flask. Under mechanical stirring at 1000 rpm, 20 mL methacrylic anhydride (MAA) was slowly added to methacrylate the lysine function groups in gelatin. The reaction was continued for 3 hours at 50° C. Crude product of GelB-MA was extracted by dripping the solution into 3 L acetone, which precipitate GelB-MA and carried away excess MAA and by-products. The GelB-MA was purified by dialysis in DI water, lyophilized, and stored at −20° C.

1.2 Synthesis of Methacrylated Hyaluronic Acid (GMHA)

The methacrylation of hyaluronic acid (HA) followed the protocol reported elsewhere [19]. In brief, 5 g of hyaluronic acid (HA) sodium salt (average MW=65,000) was dissolved by 180 mL DI water in a 250 mL round-bottom flask. 37.5 mL triethylamine and 35.5 mL glycidyl methacrylate were slowly added to the HA solution to methacrylate the hydroxyl groups of HA. The solution was stirred overnight at room temperature. GMHA was collected by precipitating the solution in 20-fold volume of acetone in the presence of a trace amount of NaCl crystals. The GMHA was purified by dialysis in DI water, lyophilizing, and stored at −20° C.

1.3 Porogen of Type-A Gelatin (GelA)

GelA was dissolved in 40° C. DPBS by 10 wt % to form GelA solution. Lecithin was dissolved in olive oil by 3 wt %. To form gelatin microparticles, 15 mL of the olive oil with lecithin was added to a 20 mL beaker, heated to 40° C., and stirred at 700 rpm by a 2-cm spinner magnet, and then 3 mL of the GelA solution was added by drops into the stirred olive oil to form a water-in-oil-phase emulsion. After 10 minutes, the stirring speed was switched to 200 rpm, and the emulsion was cooled to 5° C. by ice bath for 30 minutes. The cooling caused the gelation of GelA and the formation of GelA microparticles in olive oil. The GelA microparticles were collected by centrifuge, washed five times by 5° C. PBS, and stored at 5° C.

1.4 Porogen of GMHA

A GMHA hydrogel precursor was prepared by dissolving 10 wt % GMHA and 0.05 wt % Ir2959 in PBS. 15 mL of the aforementioned olive oil with lecithin was added to a 20 mL beaker and stirred at 700 rpm by a 2-cm spinner magnet, and 3 mL of the GMHA hydrogel precursor was added by drops into the stirred olive oil to form a water-in-oil-phase emulsion. To create GMHA hydrogel microparticles for porogen, the emulsion was exposed to ultraviolet light (365 μm, 4 mW/cm2) for 10 minutes, which polymerized GMHA and turned the droplets from the emulsion into GMHA hydrogel microparticles. The microparticles were collected and washed five times by PBS before stored at 5° C.

1.5 Acellular Alg-Ca Porogen

To prepare acellular porogen from alginate, 30 mL of the olive oil with lecithin was added to a 100 mL beaker and stirred at 1000 rpm by a 2-cm magnetic spinner, and 10 mL of 2% alginate solution in DPBS was added by drops into the stirred olive oil to form a water-in-oil emulsion. The stirring lasted for 10 minutes. To create alginate microparticles, the emulsion was rapidly mixed with 40 mL water solution of 1% CaCl2, which caused the ionic-crosslinking of alginate molecules by the calcium ions and the formation of alginate microparticles (Alg-Ca particles hereinafter). The Alg-Ca microparticles were washed five times by PBS and stored at 5° C.

1.6 Dynamic Scaffold with Single and Multiple Porogens

Prior to the fabrication of scaffolds, GelB-MA hydrogel precursor for making the framework of scaffold was prepared by dissolving 20 wt % GelB-MA plus 0.05% Ir2959 in PBS. Each type of the porogen microparticles (GelA, Alg-Ca, or GMHA) were rinsed three times by the GelB-MA precursor, and concentrated by removing excess GelB-MA precursor through a 70 μm nylon mesh, leading to a paste-like mixture (hereinafter the "porogen paste"). To prepare the dynamic scaffolds with single type of porogen (hereinafter the "mono-porogen scaffold"), the paste of such type of porogen was transferred into a polypropylene molding, which shapes the porogen paste into cylinder that are 3 mm in thickness and 5.8 mm in diameter, and was exposed to ultraviolet (UV) light (365 μm and 4 mW/cm2) for 5 minutes, causing the GelB-MA precursor crosslinked and the porogen paste turned into a hydrogel with close-packed porogen microparticles. To create a scaffold that contains three types of porogens (hereinafter the "tri-porogen scaffold"), the pastes of different porogens were mixed at equal volumes and was crosslinked following the same molding and exposure steps.

1.7 Acellular Study

Dynamic Macropore-formation in Mono-porogen Scaffolds: To understand how the GelA, Alg-Ca, and GMHA porogen microparticles individually contribute to the formation of macropores, we treated different mono-porogen scaffolds by different procedures: (1) the scaffold with GelA porogen was incubated in DPBS overnight at 37° C., a temperature that leads to the dissolving of GelA microparticles. (2) The scaffold with Alg-Ca porogen was incubated for 2 hours in a DPBS solution of 8 mM EDTA and 12 mM disodium citrate, which caused the chelating of calcium ions and subsequently the dissolving of alginate. (3) The scaffold with GMHA porogen was incubated at 37° C. for 3 hours in DPBS with 300 units/mL hyaluronidase, which digests GMHA by cleaving the β-N-acetylhexosamine-[1→4] glycosidic bonds in hyaluronic acid [20]. After the treatments, the scaffolds was rinsed by DI water 5 times and fluorescently labeled by incubation for 15 minutes in PBS with 1 mg/mL NHS-fluorescein. The morphology of each treated scaffold was studied using a Zeiss fluorescence microscope and a variable pressure scanning electron microscope (VP-SEM).

Dynamic Pore-formation in the Tri-porogen Scaffold: To understand how a sequential formation of macropores changes the morphology of scaffold in a temporal manner, we prepared the tri-porogen scaffold in triplicate and treated the scaffolds using the above three treatments by the following order—(a) incubation in 37° C. PBS overnight, (b) incubation in EDTA/disodium citrate solution for 2 hours, and (c) incubation in the hyaluronidase solution at 37° C. for 3 hours. One sample was collected after each treatment and the scaffold morphology was measure using VP-SEM.

VP-SEM Measurement: The morphology of hydrated mono- and tri-porogen scaffolds was measured using a Hitachi S-3400N VP-SEM. Samples were incubated in PBS at 37° C. overnight and rinsed by DI water before loaded to the chamber of VP-SEM. The hydrated samples were gradually cooled from room temperature to −25° C. as the chamber pressure reduced from 1 atm to 50 Pa, following a P/T curve at which water stays at liquid phase. The samples were imaged under electron-beam intensity at 15 kV and a working distance around 7 mm

1.8 Cell Study

Bovine Articular Chondrocytes (BAC):

Hyaline articular cartilage was dissected from the femoropatellar groove of two stifle joints from a three-day old calf (Research 87, Marlborough, Mass.). The cartilage was sliced into thin pieces and digested in 1 mg/mL collagenase type II and type IV in high glucose DMEM supplemented with 100 U/mL penicillin and 0.1 mg/mL streptomycin for 48 hours at 37° C. The cell suspension was filtered through a 70 μm nylon mesh, washed in DPBS and centrifuged at 460 g for 15 minutes for three times, and counted with a hemocytometer. The bovine articular chondrocytes (BACs) were expanded for two passages in chondrocyte culture medium (high glucose DMEM supplemented 10% fetal bovine serum, 10 mM HEPES, 0.1 mM nonessential amino acid, 0.4 mM L-proline, 50 μg/ml ascorbic acid, 1 mM sodium pyruvate, 100 U/mL penicillin, and 0.1 mg/mL streptomycin). To harvest the BACs at the end of each expansion, the BACs were incubated in 1 mg/mL collagenase type II and type IV in chondrocyte culture medium for 48 hours and subsequently released from the culturing flasks.

Alg-Ca Porogen that Encapsulates BACs:

In the cell study, we used Alg-Ca porogen to encapsulate BACs and later to deliver BACs into the scaffold network during the dynamic pore-formation. Since the emulsification procedure to create acellular porogen from alginate was not cell-friendly due to the association with fatty acid, surfactant and shearing stress, we created cell-laden alginate porogen microparticles using a wet-spinning process, which took place in aqueous environment. To carry out the wet-spinning, we prepared a 100 mL solution of DI water containing 0.9% NaCl and 1% CaCl2, which was filtered and transferred to a 100 mL beaker and stirred at 500 rpm by a 2-cm magnetic spinner. Passaged BACs (p2) were centrifuged and resuspended by the alginate solution (2% alginate in PBS) at 5 million cells per mL. The cell-laden solution was transferred to a syringe pump and was ejected at 0.5 mL/min through a 22G needle into the stirring salt solution, which turned the alginate solution into Alg-Ca microfibers that were 100-200 μm thick. The as-formed Alg-Ca microfibers were washed three times by the chondrocyte culture medium and minced into sub-millimeter segments, forming cell-laden Alg-Ca microparticles. The Alg-Ca microparticles were incubated in chondrocyte culture medium at 37° C. for 1 day before being incorporated into the tri-porogen scaffolds.

BAC-Laden Alg-Ca Porogen Paste:

Before being incorporated into tri-porogen scaffolds, the Alg-Ca microparticles were rinsed by the GelB-MA solution, concentrated and turned into the porogen paste following the same procedure for treating the acellular Alg-Ca.

Tri-Porogen Scaffolds with BAC-Laden Porogen:

The porogen pastes with microparticles of GelA, GMHA, and the BAC-laden Alg-Ca were mixed together at equal volume, molded and exposed for 5 minutes to UV light (365 μm, 4 mW/cm2) and became the tri-porogen scaffolds with BACs. The scaffolds were then incubated in chondrocyte culture medium at 37° C. The tri-porogen scaffolds were prepared by 48 replicates for studying the cellular behaviors of BACs in response to 3 different levels of pore-formation (to be explained) at 4 time points (day 1, 8, 15, and 21) (4 time-points×3 pore-formation levels×4 replicates per group per time-point=48 replicates). The treatments for each experimental group are list in Table 1.

Dynamic Formation of Macropores and Controlled Delivery of BACs:

The scaffolds were divided by 3 groups, and each group was treated by different sets of procedures to induce the formation of macropores to different levels (Table 1). We hypothesize that the difference at pore-formation can cause distinct cell behaviors among different groups, in terms of cell proliferation and ECM production. We induced the macropore-formations in these cell-laden scaffolds using protocols similar to treating the acellular scaffolds, except replacing PBS by chondrocyte culture medium. In brief, the treatments for inducing pore formation in the BAC-laden scaffolds became: (a) to remove GelA porogen (on day 0), the scaffolds were incubated in the culture medium at 37° C. overnight; (b) to remove Alg-Ca porogen and deliver BACs (on day 7), the scaffolds were incubate in culture medium with 8 mM EDTA and 12 mM disodium citrate at 37° C. for 2 hours; and (c) to remove the GMHA porogen (day 14), the scaffolds were incubate in culture medium with 300 units/mL hyaluronidase at 37° C. for 3 hours. Since type-A gelatin dissolved at 37° C., every group received the removal of GelA porogen on day 0. The group "EDTA-D7+HAdase-D14 group" received the removal of Alg-Ca porogen on day 7 followed by the removal of GMHA porogen on day 14. The "EDTA-D7" group received the removal of Alg-Ca porogen on day 7 but no porogen removal afterward. The "no-treatment" group was a control group receiving no porogen removal except the initial removal of GelA porogen on day 0. After each porogen removal, scaffolds were incubated three times, 15 minutes each, in 3 mL fresh culture medium to remove the treatment reagents and dissolved/digested products.

Cell Proliferation Assay Using Live/Dead Imaging:

The proliferation of BACs in the tri-porogen scaffolds was monitored using fluorescent imaging on day 1, 8, 15 and 21. Scaffolds were collected from each group, and a 200 micronthick slice was cut from the center of the scaffold for Live/Dead staining (Invitrogen). By carrying out Live/Dead imaging on the slices, we monitored the change at cell density and cell morphology in each group. Effect of cytotoxicity from the encapsulation and pore-formation was monitored based on the observed dead-cell population in the scaffolds.

Sections for Histology Analysis:

On day 21, tri-porogen scaffolds from each group were fixed in 4% paraformaldehyde overnight and stored in 70% ethanol at 4 C until processed. Scaffolds were then embedded in paraffin and processed using standard histological procedures.

H&E Staining:

H&E staining was performed according to established staining protocols [21].

Immunostaining for Collagen II and X:

For immunostaining, enzymatic antigen retrieval was performed by incubating the sections (n=3 per group per type of staining) in 0.1% Trypsin at 37° C. for 15 minutes. Sections were then blocked with blocking buffer consisting of 2% goat serum, 3% BSA and 0.1% Triton X-100 in 1×PBS, followed by incubation in rabbit polyclonal antibody to collagen type II and X (Abcam) overnight at 4° C. and secondary antibody (Alexa Fluor 488 goat anti-rabbit, Invitrogen) incubation for an hour at room temperature. Nuclei were counterstained with DAPI mounting medium (Vectashield) and images were taken with a Zeiss fluorescence microscope. Sections without primary antibody incubation were prepared as negative controls. The cell density and the collagen II and X concentrations were quantified by calculating the average fluorescence intensity per pixel using open-source program ImageJ.

1.9 Statistics

All quantitative data were expressed as mean±standard error and were verified by analysis of variance using student T-Test with equal variance. P values (two-tails) of less than 0.05 were considered statistically significant, and p values less than 0.005 were considered statistically highly significant.

2. Results 2.1 Stimulus-Induced Macropore-Formation in Mono-Porogen Scaffolds

As shown by the fluorescence images and SEM pictures (FIG. 3), the stimuli from the elevated temperature (25 to 37° C.), the presence of EDTA and the presence of hyaluronidase caused the dissolving of porogen microparticles of GelA, Alg-Ca and GMHA, respectively, and successfully induced the forming of macropores in the Gel-MA-based scaffold. As shown by the SEM pictures (FIGS. 3B, D, F), these macropores were highly interconnected and had the negative shapes of the closely-packed porogen microparticles. The GelA porogen was shown to create the most well-defined macropores, which have continuous internal surface area with micron-scaled networks formed by GelB-MA. Such micron-scaled networks were also observed from the Gel-MA hydrogels without porogen (not shown) and thus were not induced by the macropore formation. The macropores formed by the Alg-Ca and GMHA porogens have more complex shapes and contained granulated and fibrous microstructures.

2.2 Dynamic Macropore-Formation in Tri-Porogen Scaffolds

Figure 4:
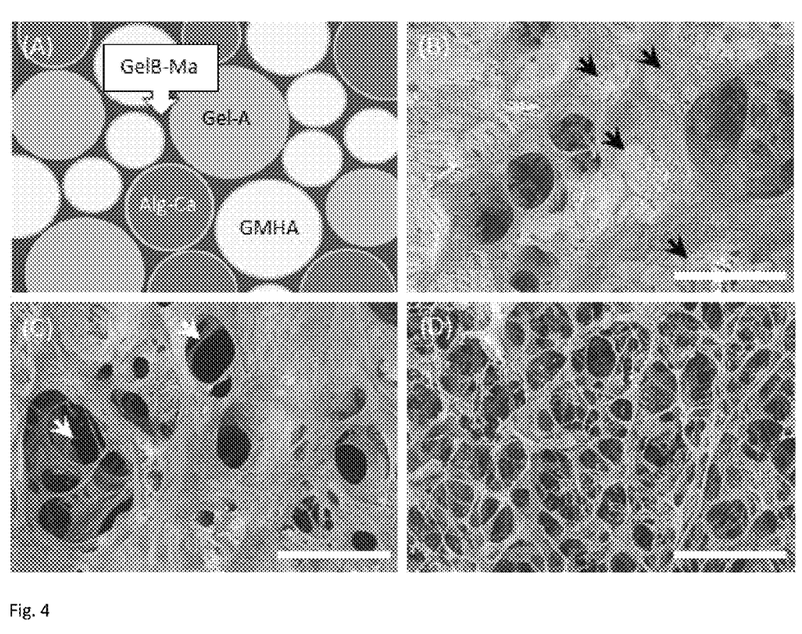
FIG. 4. A hydrogel containing three types of porogens became gradually porous after the porogens were removed by a sequence of biocompatible reagents: (A) Gel-A was removed by 37° C. PBS; (B) Alg-Ca was dissolved by EDTA; and (C) GMHA was digested by hyaluronidase. Scale bars: 200 μm.

Treating the tri-porogen scaffolds (which contained GelA, Alg-Ca and GMHA porogens) by multiple stimuli at sequential time points led to a stepwise formation of highly-interconnected macroporosity (FIG. 4A-D). The SEM picture at FIG. 4B shows that macropores began to emerge in the scaffold upon a temperature elevation from 25 to 37° C., which caused the dissolving of type-A gelatin porogen. At this stage, the macroporosity level was low and barely interconnected, as much of the scaffold volume was occupied by the porogens of Alg-Ca and GMHA, which were shown by the areas with enhanced electron scattering (the bright regions selectively indicated by dark arrows). Upon the treatment by EDTA (FIG. 4C), which carried away calcium ions and caused the Alg-Ca porogen to dissolve, the macroporosity significantly increased, became more interconnected and penetrated deeper into the scaffold volume (indicated by bright arrows). After the treatment by hyaluronidase that digested the GMHA porogen (FIG. 4D), the macroporosity became dramatically different from that of the original tri-porogen scaffold. The macropores became highly interconnected as most of the scaffold volume turned into free space. The GelB-MA volume left behind became a branched network and the whole scaffold became a gelatin-based sponge. As the stimuli were switched from EDTA to HAdase, macropores were formed in a hierarchical order that smaller pores emerged from the walls of larger pores, as shown by comparing the scaffold morphologies in FIGS. 4C and 4D.

2.3 Cell Proliferation and ECM Production in Tri-Porogen Scaffolds

Figure 5:
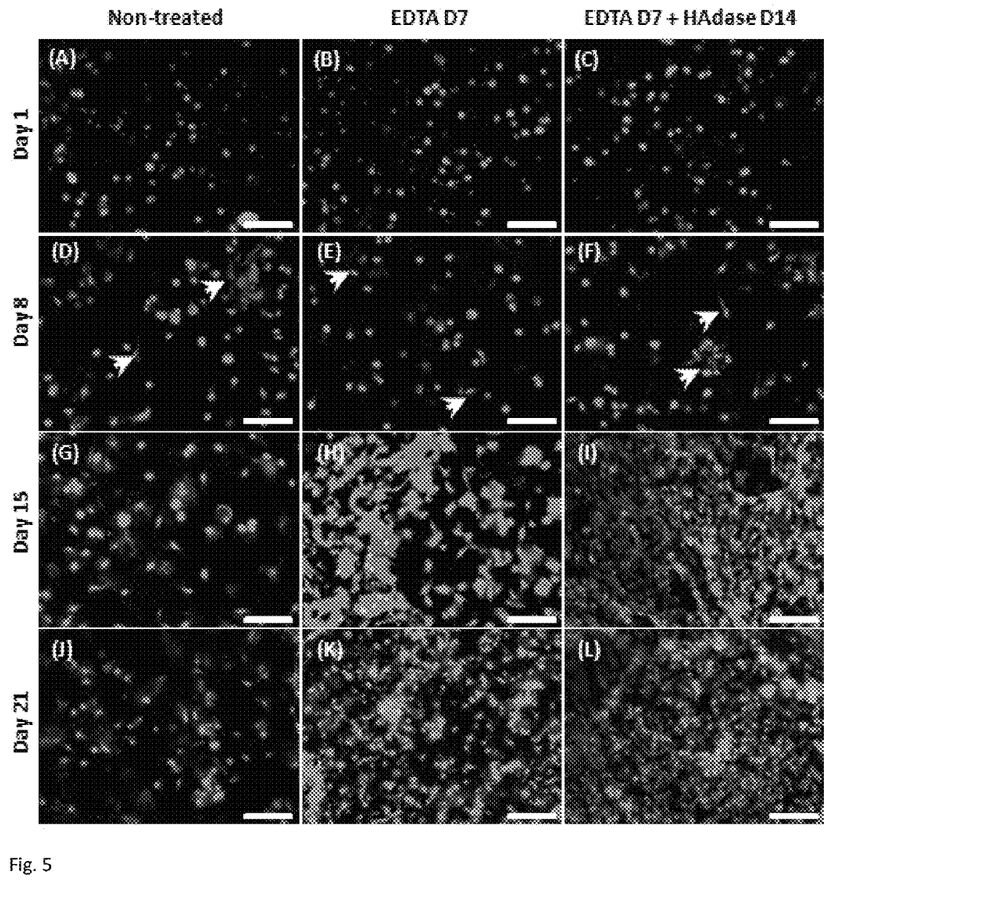
FIG. 5. Live-dead staining of cells inside the scaffolds (Live: Green, Dead: Red, Scale bar: 100 μm). Day 8: all samples showed negligible cell proli-feration. Day 15-21: the group treated by EDTA (on D7) presented significantly increased cell density. The group treated by both EDTA (on D7) and HAdase (on D14) presented higher level of cell-cell contact.

Live/Dead Fluorescence Assay:

Carrying Out Dynamic Pore-Formation on the BAC-laden, tri-porogen scaffolds led to dramatically increased BAC proliferation from day 1 to day 21. On day 1, the BACs of all groups (group Non-treated, EDTA-D7, and EDTD-D7+HAdase-D14) were encapsulated by Alg-Ca porogen and remained spherical shapes (FIG. 5A-C). The presence of dead cell population (red) indicated minor cytotoxicity effect from cell passage and encapsulation procedures. On day 8 (FIG. 5D-F), the groups treated by EDTA on day 7 (group EDTA-D7 and EDTD-D7+HAdase-D14) show no observable difference at cell-density and cell-viability in comparison with the non-treated group. However, on day 8 all groups showed slightly increased cell-spreading (indicated by arrows). On day 15 (FIG. 5G-I), the treated groups presented dramatically increased cell density, as the non-treated groups remained similar cell density. The group receiving EDTA on day 7 plus hyaluronidase on day 14 (EDTD-D7+HAdase-D14)) had similar cell density in comparison with the group receiving only EDTA (EDTD-D7), while the former showed higher level of cell-spreading and cell-cell contact than the later. The group receiving hyaluronidase on day 14 show no observable sign of cytotoxicity. On day 21 (FIG. 5J-L), both of the treated groups showed non-obvious change at cell density in comparison to day 15. The BACs in the treated groups seemed to reach confluency around day 15.

Figure 6:
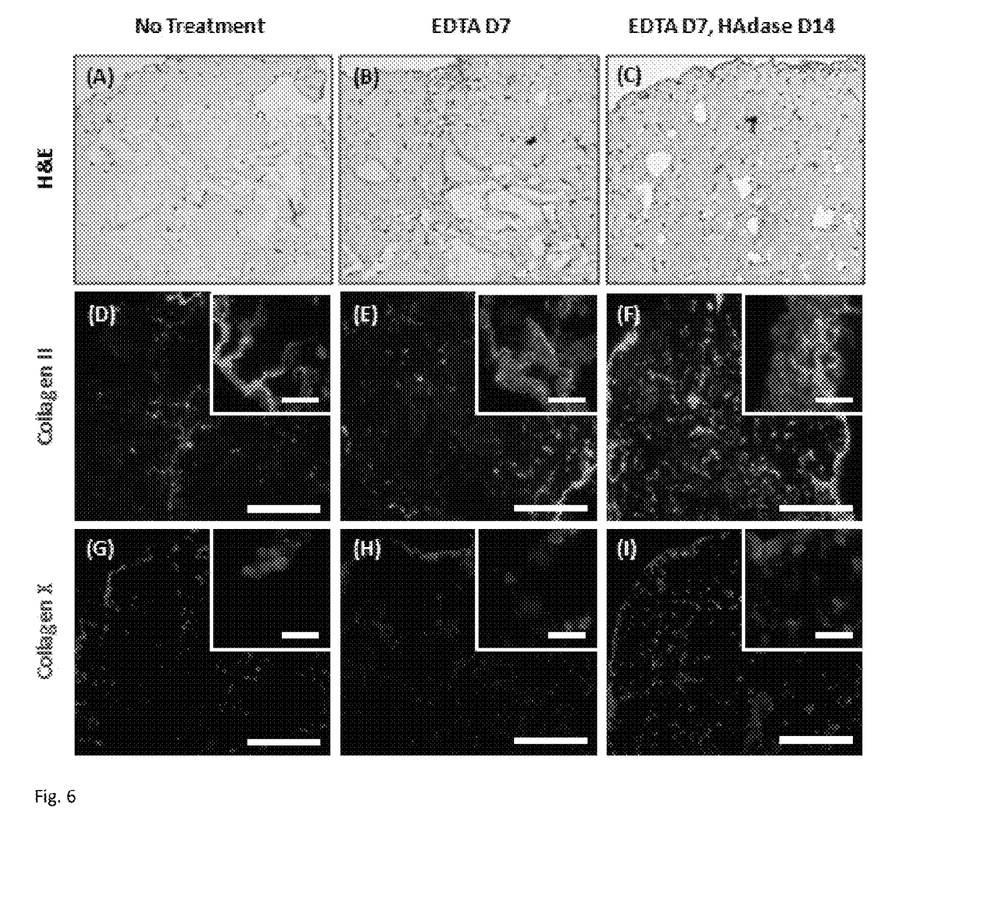
FIG. 6. Histology assays on day 21: (A-C) H&E staining showed higher ECM density in the groups treated by EDTA and HAdase. (D-I) Col-II and Col-X immunostaining showed fluorescent intensity in the groups treated by EDTA and HAdase. Scale bars: 100 μm (Inset: 15 μm).

Histology Assays:

The results from histology assays showed that the stimuli (37° C., EDTA and HAdase) treatments led to significantly higher cell density and also higher ECM concentration in the scaffold matrix. The result from haematoxylin staining showed that the tri-porogen scaffold treated by EDTA on day 7 (FIGS. 6B, C) presented significantly higher cell density than the non-treated group (FIG. 6A), a result that is consistent with the previous live/dead staining data. Eosin Y staining on day 21 (FIG. 6A-C) showed that the groups treated by all stimuli (group EDTA-D7+HAdase-D14) (FIG. 6C) presented more concentrated eosinophilic structures than the other groups (FIGS. 6A, B), suggesting a higher concentration of ECM components in this group.

The results of H&E staining were supported by the results of immunostaining, which also showed that the groups treated by EDTA had higher cell density and ECM concentration. The DAPI staining showed that the groups EDTA-D7 and group EDTA-D7+HAdase-D14 presented significantly higher density of cell nuclei than the non-treated group. The type II collagen (Col-II) assay showed significantly higher fluorescence signal in the groups treated by more stimuli (group EDTA-D7+HAdase-D14>group EDTA-D7>group Non-treated) (FIG. 6D-F). Type X collagen (Col-X) assay showed the same trend (FIG. 6 G-I). The concentration of Col-II and Col-X were shown to be positively correlated to the BAC density, as the collagen concentration tended to be highest among aggregated BACs (insets for FIG. 6D-I).

Figure 7:
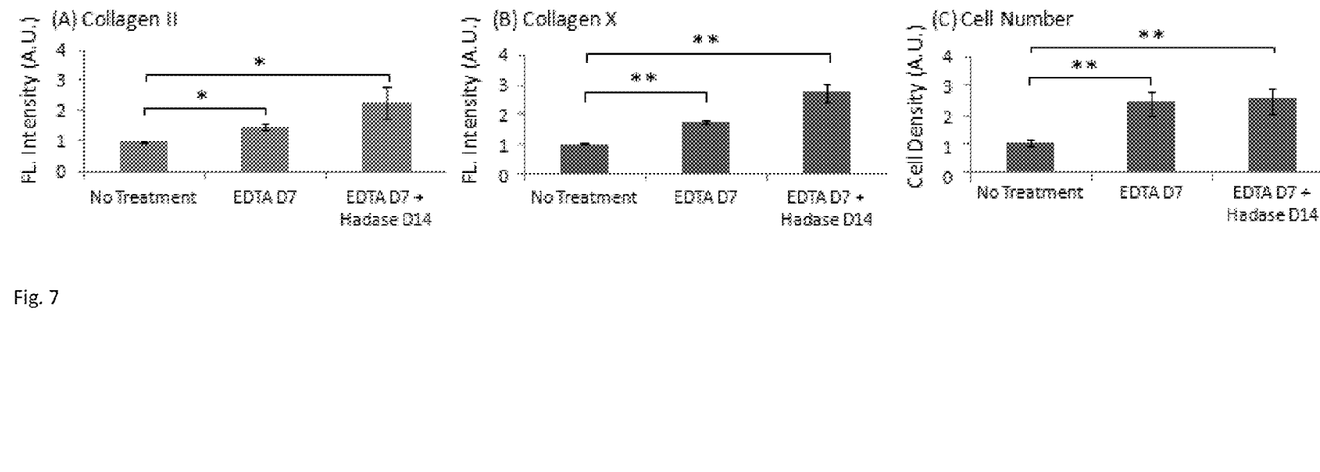
FIG. 7. Quantification based on DAPI and immunostaining result: (A) Col-II, (B) Col-X, and (C) Cell density.

Quantification based on the immunostaining results shows that treating tri-porogen scaffolds by EDTA and HAdase caused statistically significant increase at collagen concentration and cell density (FIG. 7A-C), in comparison to the non-treated scaffold. The quantified Col-II concentrations in group EDTA-D7+HAdase-D14 and group EDTA-D7 were respectively 95% (p=0.015) and 31% (p=0.020) higher than in the Non-treated group. Similarly, the quantified Col-X concentrations in group EDTA-D7+HAdase-D14 and group EDTA-D7 were respectively 173% (p<0.001) and 77% (p<0.001) higher than in the Non-treated group. Group EDTA-D7+HAdase-D14 had quantified Col-II and Col-X concentrations higher than group EDTA-D7, but the differences were not statistically significant. Both group EDTA-D7+HAdase-D14 and group EDTA-D7 had quantified cell densities significantly higher than the non-treated group by more than 140% (p<0.005), but the cell densities in these two groups were quite similar

3. Discussion

Our invention of inducing macropore-formation to assist tissue regeneration is verified by our experimental results with cellular and acellular studies. Stimuli-controlled, cell-friendly macropore-formation was successfully induced using porogens in 3D scaffolds, and significantly enhanced cell proliferation and ECM production were observed in the scaffolds with macropore-formation. To achieve these results, we have prepared the porogens and scaffolds from well-established hydrogels commonly used for tissue engineering, including gelatin, alginate, and hyaluronan derivatives. Step-wise macropore-formation in these scaffolds was achieved by inducing porogen removal with cell-friendly stimuli, including temperature change (25→37° C.), chelating molecules (EDTA) and cell-friendly enzyme (HAdase). Our method for macropore-formation is superior to many conventional methods, such as salt-leaching, freeze-drying and gas foaming, that are cytotoxic and do not allow a step-wise macropore formation in the presence of live cells.

Figure 3:
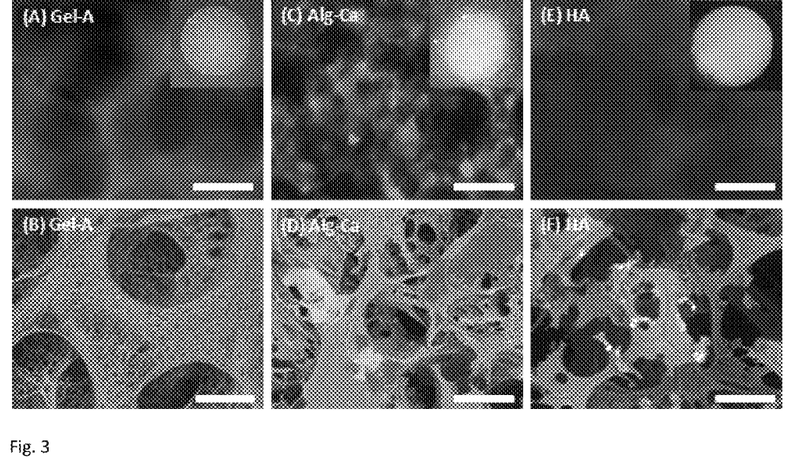
FIG. 3. Fluorescent images of three porous scaffolds developed using three different porogens (scale bars: 100 μm).

The results from mono-porogen studies showed that the porogens can be specifically removed by different stimuli to form highly interconnected macropores in a hydrogel. For tissue engineering application, this kind of macroporous structure is extremely useful in facilitating the desirable bioactivities for tissue formation, such as vascularization, cell proliferation, cell-cell interaction and ECM production. From the mono-porogen study, we found that different porogens cause distinct macropore structures (FIG. 3D-F). While the sizes of macropores were influenced by the dimensions of porogen microparticles, the morphology of internal surfaces of macropores was determined by the porogen material. In our gelatin-based hydrogel (GelB-MA), for example, gelatin (GelA) porogen led to smooth and well-defined macropores, while glycoaminoglycan (GAG)-based porogens (Alg-Ca and GMHA) led to granulated and fibrous microstructures in the macropores. Since micron-scale structures are important in influencing cell fates [22], the tailoring such surface morphology is useful to tailoring the biophysical environment and local stimuli that cells receive from the macropores.

Our invention of controlled macropore-formation was verified by sequentially treating tri-porogen scaffolds (which contain all three porogens) with stimuli specified for each porogen (FIG. 4). The scaffolds were gradually changed from non-macroporous to highly macroporous as the stimuli—37° C., EDTA and HAdase—were introduced one after another. Interesting, an hierarchical macropore-formation was observed as the stimuli were switched from EDTA to HAdase (FIGS. 4C, 4D), such phenomenon might stem from the same mechanism by which granulated and fibrous microstructures were formed by the GAG-based porogens (FIGS. 3E, 3F). In comparison with conventional porous scaffolds, this unique multi-porogen system allows us to directly control the timing and extent for remodeling the cellular microenvironment in a tissue engineering construct. While using biodegradable materials, such as (MMP)-sensitive hydrogels [23], also allows temporal changes for microenvironment, the pace of changes are subject to the bioactivities and do not offer the high controllability as our system does. In addition to the stimuli-sensitive porogens, however, we can also include biodegradable materials as one porogen type to enable cell-sensitive macropore-formation.

Our invention of controlled macropore-formation was further verified by the delivery and proliferation of neonatal BACs in the tri-porogen scaffolds. As shown by the live/dead staining data on day 1 and day 8 (FIG. 5A-F), the roughly unchanged BAC morphology and cell-density before the removal of Alg-Ca porogen (which encapsulated BACs) evidences the effective encapsulation and protection of BACs by the Alg-Ca porogen. After the delivery of BACs following Alg-Ca porogen removal on day 7, the extent of cell-spreading and the proliferation became significantly higher than the untreated control (which showed little cell proliferation from day 1 to 21), and the BACs were shown to reach confluency after about one week. Macropore-formation following Alg-Ca and GMHA porogen removal also significantly facilitated the cell production of ECM components (Col-II and Col-X), as shown by the immunostaining data on day 21 (FIGS. 7A, 7B). The materials for porogen (GelA, Alg-Ca and GMHA) and the stimuli for porogen removal (37° C., EDTA and HAdase) were proven to be non-cytotoxic. Such results verify our hypothesis that the delivery of cells by our porogen-based hydrogel is feasible, cell-friendly and able to significantly enhance cell proliferation and ECM production (as illustrated by FIGS. 1C, 1D).

The macropore-formation by Alg-Ca porogen was shown to be sufficient for cell proliferation purpose, as the quantified DAPI staining on day 21 (FIG. 7C) showed little difference at cell densities between the group treated by only Alg-Ca porogen removal and the group treated by both Alg-Ca and GMHA porogen removal. The GMHA porogen removal, however, had further enhanced the production of ECM components by BACs, as the average density of Col-II and Col-X in the group with GMHA porogen removal (EDTA-D7+HAdase-D14) was respectively 49% and 55% higher than the group without GMHA porogen removal (EDTA-D7). GMHA porogen removal also enhanced the level of cell-cell contact, as shown by a comparison between the cell morphologies in group EDTA-D7 and group EDTA-D7+HAdase-D14 on day 15 and 21 (FIG. 5H vs. 5I and FIG. 5K vs. 5L). The enhanced cell-cell contact might have contributed to the enhanced ECM production, as the immunostaining data showed that higher Col-II and Col-X densities were correlated to cell aggregation (insets of FIG. 6D-6I).

The materials and methods to approach the multi-porogen-based scaffold can be improved for better tissue engineering effect. For example, the stiffness of our tri-porogen scaffolds decreased significantly after the removal of Alg-Ca and GMHA porogens, which may limit the application of such scaffold to load-bearing implants. One way to maintain the stiffness of multi-porogen-based scaffold is by incorporating a rigid and highly porous component, such as bioabsorbable microfibers [24], for scaffold backbone. Alternatively, since the scaffold stiffness can be increased significantly overtime by the cell production of ECM (GAGs and collagens) [25], we can improve the stiffness by optimizing the timing of applying the stimuli and inducing macropore-formation when an abundance of ECM components are already produced. The choice of porogen materials is not limited to GelA, Alg-Ca and GMHA and may include any dissolvable material that is sensitive to a cell-friendly stimulus, such as MMP-sensitive polymers or photo-degradable hydrogels [13].

5. Conclusion

We have developed a novel tissue engineering scaffold undergoing cell-friendly, controllable macropore-formation. Hydrogel-based porogens were applied as templates for interconnected macropores and initial physical barrier for cell protection, and cell-friendly stimuli were applied at different time to induce specific porogen removal, causing stepwise macropore-formation and cell-delivery in the scaffold. The stimuli treatment caused no observable cytotoxicity. The macropore-formation significantly enhances cell proliferation and production of ECM components. This type of scaffold would be particularly useful to facilitate cell-based therapies by tuning the progress of macropore-formation according to the paces of cell proliferation and tissue formation.

Applications:

Our invention is designed for the application of regenerative medicine and tissue engineering in general, and can be used for the following purposes:

A 3D scaffold for in vitro cell culture/study, including cell-based drug screening in a 3D format.

A 3D platform for cell culture and expansion.

A 3D scaffold for in vitro cell culture and subsequently in vivo implantation, such as implants for skin, fat, bone, skeletomuscular, cardiovascular, and cartilage tissues.

An acellular implantation for body tissues, such as skin, fat, bone, muscle, skeletomuscular, cardiovascular, or cartilage tissues.

A drug distribution vehicle.

A cell distribution vehicle.

Advantages & Improvements Over Existing Methods, Devices or Materials:

The results from our experiments have shown our tissue engineering scaffold with dynamic macropore-formation is an outstanding biomaterial to control the microenvironment for cells in 3D. Such results evidence that the scaffold of our invention has satisfied all the important functions for a tissue engineering scaffold, as mentioned before: (1) provide cells initial protection, (2) at designable time points, provide macroporosity to facilitate mass transport, cell proliferation, and subsequent tissue formation.

In comparison to the conventional system for making tissue engineering scaffolds, our invention has the following significant improvements:

In contrast to the disadvantage of conventional hydrogel scaffolds, which contain no interconnected macroporosity and thus limit the extent of proliferation/migration of cells, the scaffold of our invention allows macropore formation at a stepwise manner, forming a biopolymer network with highly interconnected macroporosity. Such network facilitates the important bioactivities for tissue formation, including cell proliferation, migration, and producing of ECM components.

In contrast to the disadvantage of conventional macroporous scaffolds, which are unable to directly encapsulate cells in 3D and do not allow dynamic macropore-formation, using porogen units and cell-friendly stimulus for dissolving the porogen units allows us to encapsulate cells in the scaffold and temporally control the macroporosity in the cells' surrounding environment, such feature facilitates a good control of initial cell distribution in a sizable 3D scaffold.

Applications, Variations and Modifications:

A fundamental concept of our invention is to control the formation of macropores in a tissue engineering scaffold in the presence of living cells. Our invention is not limited by the above embodiment—our concept—creating a tissue engineering scaffold with controllable macropore-formation—is new in the field of regenerative medicine.

Our invention provides numerous commercial applications.

A Platform for 3D Cell Culture/Expansion:

Conventional cell expansion is carried out on a 2D surface, such as on a Petri dish. When such 2D surface is saturated by the proliferated cells (confluency), cell expansion has to be halted, with cells released by enzyme and distributed onto more culture dishes (passaged). Such change not only creates a shock that potentially affects the stability of cell phenotypes but also requires significant amount of time and labor. As the researches of cell/stem-cell based therapies are gradually developed toward large-throughput studies and clinical applications, the conventional 2D setting is causing a bottom-line cost and limitation to the companies that profit by providing cells for the research and medical institutes. In contrast to the conventional 2D setting, the dynamic macropore-formation of our invention gradually creates a large internal surface area on which cells can grow, and thus can serve as a significantly more efficient culturing platform for cell expansion.

A Scaffold for Plastic Surgery

Pysicians carrying out plastic surgeries often use 3D implants that are centimeter-thick to compensate defects. As cell-based therapies gradually become a trend in this field, it is important to provide physicians a choice to use a 3D biomaterial that facilitates bioactivities which lead to host-tissue formation, such as vascularization, cell migration, cell proliferation, and cell producing of ECM components. To achieve such purposes, it is very important to include following features in such implantation: (1) sufficient macroporosity in the scaffold, (2) good cell distribution, and (3) initial protect for cells against the host environment. As demonstrated by our experimental results, the current invention can effectively support such features.

REFERENCES

[1] Hong Y, Guan J, Fujimoto K L, Hashizume R, Pelinescu A L, Wagner W R. Tailoring the degradation kinetics of poly (ester carbonate urethane)urea thermoplastic elastomers for tissue engineering scaffolds. Biomaterials. 2010; 31(15):4249-58. (PMID: 20188411)

[2] Mondrinos M J, Dembzynski R, Lu L, Byrapogu V K, Wootton D M, Lelkes P I, et al. Porogen-based solid free-form fabrication of polycaprolactone-calcium phosphate scaffolds for tissue engineering. Biomaterials. 2006; 27(25):4399-408. (PMID: 16678255)

[3] Chen V J, Ma P X. Nano-fibrous poly(L-lactic acid) scaffolds with interconnected spherical macropores. Biomaterials. 2004; 25(11):2065-73. (PMID: 14741621)

[4] Salerno A, Guarnieri D, Iannone M, Zeppetelli S, Netti P A. Effect of micro- and macroporosity of bone tissue three-dimensional-poly(epsilon-caprolactone) scaffold on human mesenchymal stem cells invasion, proliferation, and differentiation in vitro. Tissue Eng Part A. 2010; 16(8): 2661-73. (PMID: 20687813)

[5] Xiao J, Duan H, Liu Z, Wu Z, Lan Y, Zhang W, et al. Construction of the recellularized corneal stroma using porous acellular corneal scaffold. Biomaterials. 2011; 32(29):6962-71. (PMID: 21719100)

[6] Jang J H, Castano O, Kim H W. Electrospun materials as potential platforms for bone tissue engineering. Adv Drug Deliv Rev. 2009; 61(12):1065-83. (PMID: 19646493)

[7] Gauvin R, Chen Y C, Lee J W, Soman P, Zorlutuna P, Nichol J W, et al. Microfabrication of complex porous tissue engineering scaffolds using 3D projection stereolithography. Biomaterials. 2012; 33(15):3824-34. (PMID: 22365811)

[8] Fozdar D Y, Soman P, Lee J W, Han L H, Chen S. Three-Dimensional Polymer Constructs Exhibiting a Tunable Negative Poisson's Ratio. Adv Funct Mater. 2011; 21(14): 2712-20. (PMID: 21841943)

[9] Fierz F C, Beckmann F, Huser M, Irsen S H, Leukers B, Witte F, et al. The morphology of anisotropic 3D-printed hydroxyapatite scaffolds. Biomaterials. 2008; 29(28):3799-806. (PMID: 18606446)

[10] Hollister S J. Porous scaffold design for tissue engineering. Nat Mater. 2005; 4(7):518-24. (PMID: 16003400)

[11] Ovsianikov A, Schlie S, Ngezahayo A, Haverich A, Chichkov B N. Two-photon polymerization technique for microfabrication of CAD-designed 3D scaffolds from commercially available photosensitive materials. J Tissue Eng Regen Med. 2007; 1(6):443-9. (PMID: 18265416)

[12] Lyons F G, Al-Munajjed A A, Kieran S M, Toner M E, Murphy C M, Duffy G P, et al. The healing of bony defects by cell-free collagen-based scaffolds compared to stem cell-seeded tissue engineered constructs. Biomaterials. 2010; 31(35):9232-43. (PMID: 20863559)

[13] Lutolf M P, Lauer-Fields J L, Schmoekel H G, Metters A T, Weber F E, Fields G B, et al. Synthetic matrix metalloproteinase-sensitive hydrogels for the conduction of tissue regeneration: engineering cell-invasion characteristics. Proc Natl Acad Sci USA. 2003; 100(9):5413-8. (PMID: 12686696)

[14] Kraehenbuehl T P, Ferreira L S, Zammaretti P, Hubbell J A, Langer R. Cell-responsive hydrogel for encapsulation of vascular cells. Biomaterials. 2009; 30(26):4318-24. (PMID: 19500842)

[15] Moss J A, Stokols S, Hixon M S, Ashley F T, Chang J Y, Janda K D. Solid-phase synthesis and kinetic characterization of fluorogenic enzyme-degradable hydrogel crosslinkers. Biomacromolecules. 2006; 7(4):1011-6. (PMID: 16602715)

[16] Nichol J W, Koshy S T, Bae H, Hwang C M, Yamanlar S, Khademhosseini A. Cell-laden microengineered gelatin methacrylate hydrogels. Biomaterials. 2010; 31(21):5536-44. (PMID: 20417964)

[17] Khalil S, Sun W. Bioprinting endothelial cells with alginate for 3D tissue constructs. J Biomech Eng. 2009; 131(11):111002. (PMID: 20353253)

[18] Burdick J A, Chung C, Jia X, Randolph M A, Langer R. Controlled degradation and mechanical behavior of photopolymerized hyaluronic acid networks. Biomacromolecules. 2005; 6(1):386-91. (PMID: 15638543)

[19] Suri S, Schmidt C E. Cell-laden hydrogel constructs of hyaluronic acid, collagen, and laminin for neural tissue engineering. Tissue Eng Part A. 2010; 16(5):1703-16. (PMID: 20136524)

[20] Maksimenko A V, Schechilina Y V, Tischenko E G. Role of the glycosaminoglycan microenvironment of hyaluronidase in regulation of its endoglycosidase activity. Biochemistry (Mosc). 2003; 68(8):862-8. (PMID: 12948386)

[21] Bonifacino J S, Dasso M, Harford J B, Lippincott-Schwartz J, Yamada K M. Short Protocols in Cell Biology. Hoboken, N.J.: John Wiley & Sons, Inc.; 2004. ch. 2, p. 16.

[22] Raines A L, Olivares-Navarrete R, Wieland M, Cochran D L, Schwartz Z, Boyan B D. Regulation of angiogenesis during osseointegration by titanium surface microstructure and energy. Biomaterials. 2010; 31(18):4909-17. (PMID: 20356623)

[23] Anderson S B, Lin C C, Kuntzler D V, Anseth K S. The performance of human mesenchymal stem cells encapsulated in cell-degradable polymer-peptide hydrogels. Biomaterials. 2011; 32(14):3564-74. (PMID: 21334063)

[24] Huttunen M, Kellomaki M. A simple and high production rate manufacturing method for submicron polymer fibres. J Tissue Eng Regen Med. 2011; 5(8):e239-43. (PMID: 21485008)

[25] Sampat S R, O'Connell G D, Fong J V, Alegre-Aguaron E, Ateshian G A, Hung C T. Growth factor priming of synovium-derived stem cells for cartilage tissue engineering. Tissue Eng Part A. 2011; 17(17-18):2259-65. (PMID: 21542714)

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method for making a macroporous 3-D tissue engineering scaffold from an article comprising multiple distinct macroparticulate porogens and living cells distributed within a polymer scaffold, wherein the porogens are selectively and sequentially dissolvable by corresponding distinct biocompatible stimuli, comprising: sequentially contacting the article with said distinct biocompatible stimuli, wherein each of the porogens is selectively and sequentially dissolved by the corresponding biocompatible stimulus, thereby temporally and spatially controllably forming macropores within the polymer scaffold, wherein the tissue engineering scaffold is formed.

2. The method of claim 1 wherein the polymer is a natural polymer selected from a protein, a polypeptide, a polynucleotide, a natural resin, a rubber, and a polysaccharide, or a synthetic polymer selected from polystyrene, polypropylene, polyvinyl chloride, polyether, polyester, polyamide, polyimide, and organosilicon compound, or a combination thereof.

3. The method of claim 1, wherein the polymer is a natural polymer selected from fibrin, fibrinogen, fibronectin, collagen, gelatin, dextran, chondroitin sulfate, alginate, chitosan, chitin, hyaluronic acid, heparin sulfate, a protein, a nucleotide, a polysaccharide, and a glycosaminoglycan.

4. The method of claim 1, wherein the polymer is synthetic polymer selected from poly (ethylene glycol), poly(lactic-co-glycolic acid), poly (glycolic acid), poly (lactic acid), polycaprolactone, poly(methyl methacrylate), polyurethane, and a silicone.

5. The method of claim 1, wherein the polymer is modified gelatin comprising cross-linked methacrylate functional groups.

6. The method of claim 1 wherein each of the porogens comprises gelatin, hyaluronic acid, or alginate.

7. The method of claim 1 wherein each of the stimuli is a change in one or more of temperature, pH, ionic strength, electromagnetic radiation exposure, enzyme activity, chelator activity and mechanical agitation.

8. The method of claim 1 wherein the article comprises three distinct macroparticulate porogens, and the method comprises sequentially contacting the article with corresponding three distinct stimuli.

9. The method of claim 1 wherein the article comprises three distinct macroparticulate porogens and the method comprises sequentially contacting the article with corresponding three distinct stimuli, wherein the three distinct porogens comprise gelatin, hyaluronic acid and alginate, respectively, and the three distinct stimuli are a change in temperature, a change in EDTA chelator activity and a change in hyaluronidase enzyme activity, respectively, and wherein the polymer is modified gelatin comprising cross-linked methacrylate functional groups.

10. The method of claim 1 wherein the article comprises three distinct macroparticulate porogens and the method comprises sequentially contacting the article with corresponding three distinct stimuli, wherein the three distinct porogens comprise gelatin, hyaluronic acid and alginate, respectively, and the three distinct stimuli are a change in temperature, a change in EDTA chelator activity and a change in hyaluronidase enzyme activity, respectively, and wherein the polymer is modified gelatin comprising cross-linked methacrylate functional groups, and the cells are chondrocytes.

11. The method of claim 1, wherein the macropores have average pore size in the range 10-500 μm.

12. The method of claim 1, wherein the density of the cells does not decrease with distance from a surface of the article.

13. The method of claim 1, wherein the tissue engineering scaffold is at least 1 cm$^3$ in volume.

14. The method of claim 1, wherein the tissue engineering scaffold comprises bioactive ligands that specifically interact with biomolecules of the cells or bind biomolecules that interact with the biomolecules of the cells, to direct cell fate or induce the cells to form a tissue, the ligands being selected from the group consisting of carboxyl, amine, phenol, guanidine, thiol, indole, imidazole, hydroxyl, sulfate, norbornene, maleimide, laminin, fibronectin, fibrinogen, peptide sequences, and combinations thereof.

15. The method of claim 1, wherein the porogens have the shape of a sphere, an ellipsoid, a polyhedron, a cube, a rod, a cylinder, a sheet, a fiber, a ribbon, a helix, or a ring.

16. The method of claim 1, wherein the tissue engineering scaffold is saturated with a cell growth medium.

17. The method of claim 1, wherein the article is an implant in a body, and the sequential contacting and macropore formation occur inside the body.

18. The method of claim 1, wherein the article is an implant in a body, and the sequential contacting and macropore formation occur inside the body, wherein the method promotes growth of skin, fat, bone, muscle, skeletomuscular, cardiovascular, or cartilage tissue of the body.

19. The method of claim 1, wherein the tissue engineering scaffold is loaded with a drug and shaped as drug distribution vehicle.

20. The method of claim 1, wherein:
a) the tissue engineering scaffold has a density in the range 2.5 to 10% (wt/v);
b) the tissue engineering scaffold has a tunable compressive modulus from 0.3 kPa to 100 kPa
c) the tissue engineering scaffold sustains 90% strain and 35 MPa stress without failing;
d) the tissue engineering scaffold maintains more than 50% strain energy after being exposed to 60, 70% cyclic compressions,
e) the tissue engineering scaffold maintains more than 50% compressive modulus at 20-30% strain after receiving 80% cyclic compressions;
e) the tissue engineering scaffold visually reverses to its original shape after receiving 90% cyclic-strain; or
f) as compression on the tissue engineering scaffold increases up to 90%, the density increases, and the compressive modulus of the tissue engineering scaffold increases non-linearly from 20 kPa to 35,600 kPa.

* * * * *